United States Patent [19]

Garzaran

[11] Patent Number: 5,187,177
[45] Date of Patent: Feb. 16, 1993

[54] METHOD AND A PHARMACEUTICAL PREPARATION FOR TREATING PAIN

[75] Inventor: Jose P. Garzaran, Barcelona, Spain

[73] Assignee: Novo Nordisk A/S, Bagsvaerd, Denmark

[21] Appl. No.: 672,546

[22] Filed: Mar. 21, 1991

[51] Int. Cl.$^5$ .............................................. A61K 31/44
[52] U.S. Cl. ................................................... 514/282
[58] Field of Search ........................................ 514/282

[56] References Cited

PUBLICATIONS

Chem. Abst. 102-143,589J (1985).

*Primary Examiner*—S. J. Friedman
*Attorney, Agent, or Firm*—Fidelman & Wolffe

[57] ABSTRACT

A method of relieving pain comprises administering, to the subject suffering from the pain, a pharmaceutically effective amount of glucagon and a spasmogenic analgesic. A ratio of 0.1–10 parts of glucagon per 10 parts of analgesic is administered.

Furthermore, the use of glucagon for the preparation of a pharmaceutical preparation for treating pain is disclosed.

5 Claims, No Drawings

METHOD AND A PHARMACEUTICAL PREPARATION FOR TREATING PAIN

BACKGROUND TO THE INVENTION

The present invention relates to a method and a pharmaceutical preparation for treating pain, especially colic pain such as biliary colic pain.

Treating biliary colic pain is extremely difficult as the use of spasmogenic analgesics such as opioids is undesirable and contraindicated due to their spasmogenic action on the biliary tract particularly at the sphincter of Oddi, and thus the spasmogenic analgesics worsen the pain rather than alleviating the same.

According to Jaffe J. H., Martin W. R., Opioid analgesic and antagonists. In: Goodman A., Goodman L. S.; Gilman A. (eds) the Pharmacological Basis of Therapeutics. New York 1980; Macmillan Publishing Co.: 494–534. (Pages 504–505), therapeutic doses of spasmogenic analgesics, particularly of morphine, or codeine, and other morphine surrogates, can cause a marked increase in pressure in the biliary tract. Some patients with biliary colic pain may experience exacerbation and not relief of pain when given these drugs. Furthermore, an occasional individual complains of pain in the epigastrium or right hypochondrium after administration of morphine, probably due to duodenal or biliary tract spasm. Spasm of the biliary tract produced by morphine is evident roentgenographically as well as manometrically, and a sharp constriction becomes apparent at the lower end of the common bile duct (sphincter of Oddi). This spasm prevents emptying and thus causes the intraductal pressure to rise.

In Martindale, The Extra Pharmacopoeia. Reynolds J. E. F. (ed). 28th edition, London 1982: The Pharmaceutical Press. Pg. 1020 this spasmogenic action of the alkaloid opiates (morphine and morphinelike substances) is also pointed out.

Other therapeutic approaches have been the use of anticholinergic agents as spasmolytic substances, which have been widely employed but on an empirical basis, because there is no conclusive evidence that they are efficient.

Glucagon has been shown to be efficient in relieving biliary colic pain in several studies (see Paul F, The role of glucagon in the treatment of biliary tract pathology. In: Picazo J. (ed) Glucagon in Gastroenterology. Lancaster 1979; MTP Press: 10–120; Brandstätter G., Kratochvil P., Glukagon Bei Gallenkoliken. Therapiewoche 1979; 29:3362–3365), (see also Hard-castle J. D., Stower M. J., Foster G. E., The use of glucagon in spastic disorders of the gastrointestinal tract. In: Picazo J. (ed) Glucagon in Gastroenterology and Hepatology. Pharmacological, Clinical, and Therapeutic Implications. Lancaster 1982; MTP Press: 115–125; Stower M. J., Foster G. E., Hardcastle J. D., a trial of glucagon in the treatment of biliary tract disease. Br J. Surg 1982; 69:591–592; Grossi E., Broggini M., Quaranta M., Balestrino E., Different pharmacological approaches to the treatment of acute biliary colic. Curr Ther Res 1986; 40:876–882). However, the relief of pain is not as immediate as is desirable. The same thing applies to the results obtained with the use of prostaglandin synthesis inhibitors, i.e., diclofenac sodium (Grossi et al., ibid).

Glucagon is known to reverse the biliary spasm induced by administration of narcotics in man (Bordley J., Olson J. E., The use of glucagon in operative cholangiography. Surg Gynecol Obstet 1979; 149:583–584; Jones R. M., Fiddian-Green R., Knight P. R., Narcotic-induced choledochoduodenal sphincter spasm reversed by glucagon. Anesth Analg 1980: 59:946–947; Jones R. M., Coultas R. J., Pollard B. J., Waterland J. W., Reversal of biliary sphincter spasm with low dose Glucagon during operative cholangiography. Anaesth Intens Care 1983; 11:1174–175; McCammon R. L., Stoelting R., Madura J. A., Reversal of fentanyl induced spasm of the sphincter Oddi. Surg Gynecol Obstet 1983; 156:326–334; and Setakis N., Economou J., Ritsi N., Konidis A., Georgiadis N., Andoniou G., Effect of cimetidine, glucagon, propantheline bromide, morphine, pethidine, naloxone, ethyl alcohol on sphincter of Oddi (Abst). Gut 1990; 31: A488). McCammon et al. have demonstrated this by radio manometric methods and Carr-Locke and Gregg by endoscopic manometry. According to Carr-Locke D. L., see Glucagon and the human biliary tree. In: Picazo J. (ed) Glucagon in 1987. Gastrointestinal and Hepatobiliary Physiology, Diagnosis and Treatment. Lancaster 1987; MTP Press: 67–86 (Pages 76–79, 85), glucagon is an inhibitor of gastrointestinal motility, and glucagon would seem to have opposing effects to opiates, i.e., morphine. In his study, the spasm induced by the intravenous administration of 5 mg morphine was reversed 2 minutes after the intravenous injection of 1 mg Glucagon. This is believed to suggest that spasmogenic analgesics, particularly the opiate alkaloids and notably morphine and glucagon either share a common receptor site or share some common pathway of smooth muscle cell control perhaps through their known effects in intracellular cyclic nucleotides.

All the above evidence explains why use of spasmogenic analgesics are contraindicated for treatment of biliary colic pain. However, due to the high efficiency analgesic effects of opioides it is very desirable to have available the possibility to utilize them in relieving pain in patients suffering from biliary colic pain.

BRIEF DESCRIPTION OF THE INVENTION

The present invention relates to a method of relieving pain through the administration of glucagon and a spasmogenic analgesic and to a pharmaceutical preparation comprising glucagon and a spasmogenic analgesic adapted for treating pain.

DETAILED DESCRIPTION OF THE INVENTION

The present invention relates, according to a first aspect thereof, to a method of relieving pain comprising administering to a subject suffering from pain a pharmaceutically effective amount of glucagon and a spasmogenic analgesic. The method is preferably used to treat acute biliary colic pain as such. Administration of glucagon together with the spasmogenic analgesic releases the biliary spasm without blocking the analgesic effect of the analgesic, and a quick relief of the pain can be obtained thereby.

It has been alleged that in combination with surgery, glucagon maybe used to reverse the spasms of the sphincter of Oddi without counteracting the analgesic effect of narcotics (McCammon et al., 1983 and Carr-Locke, 1987) but no experimental support is provided for such allegations.

According to the present invention it has been shown that glucagon in proportions of 0.1–10 parts per 10 parts by wt. of spasmogenic analgesic depending on the analgesic in question reverses the spasmogenic effect of opioids without blocking their analgesic effect, allowing thereby for the use thereof to treat biliary colic pain, and thus a quick relief of the pain can be achieved.

The alkaloid narcotics which may be used in accordance with the present invention are analgesic e.g. opiates such as morphine, nicomorphine, fentanyl, mepiridine, alfentanile, pethidine, ketobemidon, dextromoramide, or methadone.

In practice of the method of the invention, glucagon and the analgesic may be administered in manners conventional for giving the analgesic treatment, e.g., in the form of subcutaneous injection separate preparations. Intravenous administration of both preparations may be employed. Oral dosage unit forms are contemplated.

According to one mode of the invention the glucagon and the spasmogenic analgesics are administered in the form of separate preparations one immediately after each other, in which case it is preferred to parenterally administer the glucagon first and then the analgesic so as to avoid any spasmogenic effect by the analgesic.

According to another aspect of the invention, a narcotic is used in a pharmaceutical preparation for treating biliary colic pain.

Typically, the glucagon containing pharmaceutical preparation for relieving pain is prepared by mixing glucagon, optionally in combination with a pharmaceutically acceptable carrier, with suitable excipients for lyophilizing and lyophilizing the resulting mixture, as has been done heretofore for the known indications of glucagon usage. Thus, for example, the glucagon may be formulated so as to be administered at a rate of 1 mg per 70 kg of body weight.

Thus, an exemplary preferred mode of practice of this invention contemplates administration of a commercially available morphine sulfate solutions as recommended by the supplier, such as for example subcutaneous administration of an 8 mg, 10 mg or 15 mg of morphine dosage unit (Astra) or 10 mg dosage unit (Elkins-Sinn) or alternatively either a 10 or 20 mg of morphine dosage unit oral solution or 15 or 30 mg of morphine dosage unit tablet (Roxanne) preceded immediately (i.e., within five minutes) by parenteral, e.g., subcutaneous administration of a solution of a 1 mg dosage unit of glucagon hydrochloride dissolved in distilled water, pH adjusted to pH 3.5 or of a commercially available 1 mg dosage unit glucagon.

The glucagon used in accordance with the present invention is preferably human glucagon and may be derived from a natural source, i.e., being extracted and purified from pancreas, or prepared using genetically transformed microorganisms, preferably yeast, e.g., as described in EP A 189,998. The glucagon should be pure enough to yield a single major band on the polyacryl amide gel.

All told, the pain relieving pharmaceutical preparations comprising glucagon and analgesic to be administered separately according to the present invention may each be of a composition known per se and be prepared in a manner known per se for the preparation of the corresponding known analgesic and glucagon preparations.

What is claimed is:

1. A method of relieving pain in a subject suffering from biliary colic pain comprising administering to the said subject suffering from biliary colic pan a pharmaceutically effective amount of glucagon and a pharmaceutically effective amount of a spasmogenic analgesic at about the same time in a ratio of about 0.1–10 parts of glucagon per 10 parts of spasmogenic analgesic.

2. A method as claimed in claim 1 wherein the spasmogenic analgesic is a narcotic opiate-like substance selected from the group consisting of morphine, nicomorphine, fentanyl, mepiridine, alfentanile, pethidine, ketobemidon, dextromoramide, and methadone.

3. A method as claimed in claim 2 wherein the spasmogenic analgesic is morphine.

4. A method according to claim 1 wherein the glucagon is administered parenterally in an amount of about 1 mg.

5. A method as claimed in claim 3, wherein morphine, is administered orally or subcutaneously in an amount of 8, 10, 15, 20, or 30 mg.

* * * * *